United States Patent [19]

Goemans

[11] Patent Number: Plant 7,079

[45] Date of Patent: Dec. 19, 1989

[54] ALSTROEMERIA PLANT NAMED CAVALIER

[75] Inventor: Frank Goemans, Chichester, England

[73] Assignee: Wuelfinghoff Freesia B.V., Netherlands

[21] Appl. No.: 294,261

[22] Filed: Jan. 6, 1989

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An Alstroemeria plant named Cavalier, having white flowers with blotches of pink, particularly in outer petals, and inner petals which are infused with a bright yellow and have dark brown streaks of medium size extending throughout the infused area.

1 Drawing Sheet

1

The present invention comprises a new and distinct cultivar of Alstroemeria plant known by the cultivar name Cavalier.

Cavalier was originated by the inventor Frank Goemans from a hybridization made in a controlled breeding program in Chichester, Sussex, United Kingdom in 1984. The female parent was a cultivar designated N. 68, an unnamed cultivar of unknown origin. The male parent of Cavalier was a cultivar designated 21, a hybrid derived from *A. Violacea.*

Cavalier was discovered and selected as one flowering plant within the progeny of the stated parentage by Frank Goemans on June 6, 1984 in a controlled environment in Chichester, United Kingdom.

The first act of asexual reproduction of Cavalier was accomplished when vegetative cuttings were taken from the initial selection on June 30, 1984 in a controlled environment in Chichester, United Kingdom by Frank Goemans. Horticultural examination of selected units initiated June 27, 1986 has demonstrated that the combination of characteristics as herein disclosed for Cavalier are firmly fixed and retained through generations of asexual reproduction.

Cavalier has not been observed under all possible environmental conditions. The phenotype may vary significantly with variations in environment such as temperature, light intensity and day length. The following observations, measurements and comparisons describe plants grown in Spalding Lincs, United Kingdom under greenhouse conditions which approximate those generally used in commercial practice.

The following traits have been repeatedly observed and are determined to be basic characteristics of Cavalier which in combination distinguish this Alstroemeria as a new and distinct cultivar:

1. The base color of the flowers is white to pale pink, with dark pink blotches in the outer petals.

2. The upper surfaces of the inner petals are bright yellow at the base and continuing outwardly, with the outer ends of the inner petals being a purplish pink similar to the outer petals.

3. The inner petals have brown streaks of medium length on their upper surface.

The accompanying photographic drawing shows typical inflorescence and foliage characteristics of Cavalier, with colors being as nearly true as possible with illustrations of this type. The photograph comprises a closeup view of a flower in bloom, buds, and foliage.

2

In the following description, color references are made to The Royal Horticultural Society Color Chart. The color values were determined in the afternoon of May 21, 1986 under natural light conditions at Spalding, United Kingdom.

Classification:

*Botanical.*—Alstroemeria cv Cavalier.

*Commercial.*—Alstroemeria.

PLANT

Form: Medium.

Height: Typically reaches 50 inches.

Growth: Strong.

Foliage:

*Quantity.*—Medium.

*Size of leaf.*—Medium, 6×1.5 inches.

*Shape of leaf.*—Broadly obovate.

*Color.*—Upperside and underside are dark green.

Rhizomes:

*Color.*—White.

*Size.*—Normal.

INFLORESCENCE

A. Bud

*Form.*—Normal.

*Diameter.*—One-half inch.

*Length.*—One and one-half inch.

*Calyx.*—Broadly elliptic.

B. Flower

*Size.*—3 inches in diameter

*Borne.*—Medium number of branches in umbel

*Blooming habit.*—Medium

*Shape.*—Normal, inner petals, obovate

*Color.*—Upper surface: 155D with blotches of pink shading through on outer and inner petals; inner petals are heavily infused with yellow 14A-B from adjacent base to an area spaced from petal tip, with dark brown streaks appearing throughout the upper surface of the inner petals; Under surface: 155D with blotches of bright pink 68A-B on all petals; smaller, inner petals infused with areas of 10B.

*Peduncle.*—Length 50 inches, color medium green.

*Lasting quality.*—Approximately 10 days.

REPRODUCTIVE ORGANS

Stamens: Number, 6.

Anthers: Color, yellow-green.
Filaments: Color, purple-pink.
Pistils: Number, 1; Color, purple-pink.
Stigma: Color, cream.

I claim:

1. A new and distinct cultivar of Alstroemeria named Cavalier, as illustrated and described.

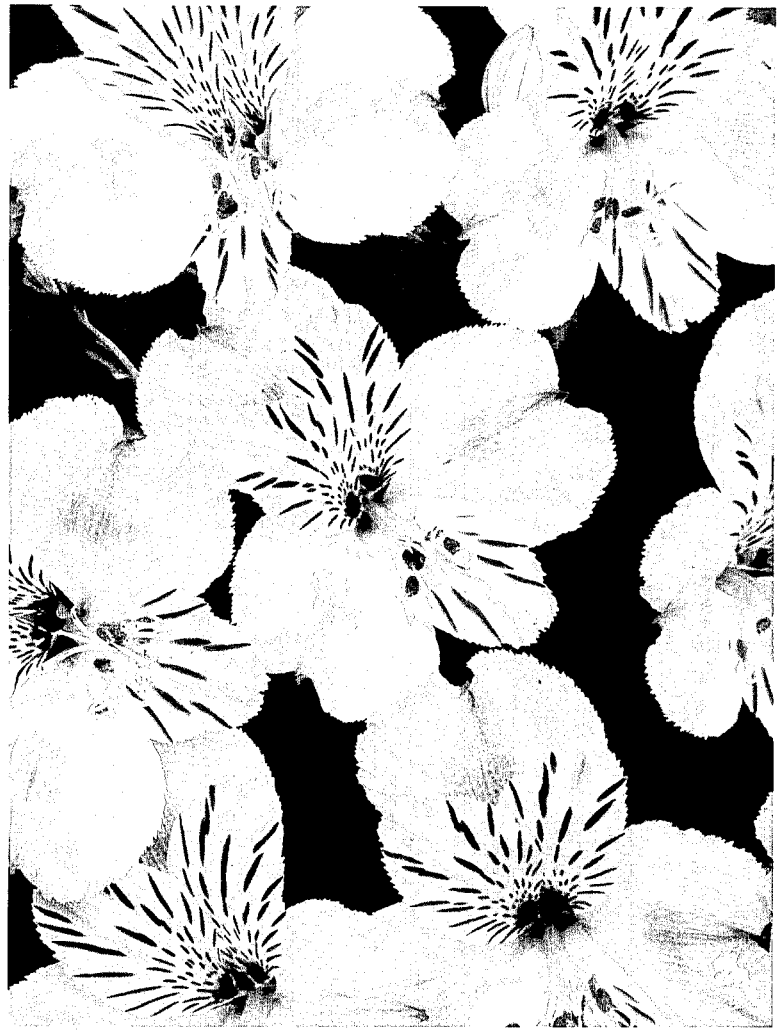

* * * * *